United States Patent [19]

Austin

[11] Patent Number: 5,435,999
[45] Date of Patent: Jul. 25, 1995

[54] PROLIFERATIVE ACTION OF LEUKAEMIA INHIBITORY FACTOR ON SATELLITE CELLS

[75] Inventor: Lawrence Austin, Mount Waverley, Australia

[73] Assignee: Monash University, Clayton, Australia

[21] Appl. No.: 741,522

[22] PCT Filed: Nov. 20, 1990

[86] PCT No.: PCT/AU90/00556
§ 371 Date: Aug. 12, 1991
§ 102(e) Date: Aug. 12, 1991

[87] PCT Pub. No.: WO91/07992
PCT Pub. Date: Jun. 13, 1991

[30] Foreign Application Priority Data
Nov. 24, 1989 [AU] Australia ............... PJ7552/89

[51] Int. Cl.$^6$ .................. A61K 35/34; A61K 38/19; C12N 5/08
[52] U.S. Cl. .................. 424/93; 435/240.2; 514/2
[58] Field of Search ............ 435/240.2, 240.21; 530/351; 424/93 U; 514/2

[56] References Cited
U.S. PATENT DOCUMENTS
5,166,065 11/1992 Williams et al. ............... 435/240.1

FOREIGN PATENT DOCUMENTS
8800093 10/1988 Australia .

OTHER PUBLICATIONS

Baumann, et al.; Journal of Immunology, vol. 143, pp. 1163–1167; Aug. 15, 1989.
Baumann, et al. (1989) "Hepatocyte-Stimulating Factor III Shares Structural and Functional Identity with Leukemia-Inhibitory Factor", *J. Immunol.* 143, 1163–1167.
Yamamori et al. (1989) "The Cholinergic Neuronal Differentiation Factor From Heart Cells Is Identical to Leukemia Inhibitory Factor" *Science* 246, 1412–1416.

*Primary Examiner*—George C. Elliott
*Attorney, Agent, or Firm*—Scully, Scott, Murphy & Presser

[57] ABSTRACT

The present invention relates to the use of leukaemia inhibitory factor (LIF), alone or in combination with other cytokines such as interleukin-6 (IL-6) and/or transforming growth factor $\alpha$(TGF$\alpha$) and/or fibroblast growth factor (FGF), to stimulate the proliferation and/or differentiation of mammalian satellite cells. The present invention also contemplates a method comprising myoblast transfer therapy whereby LIF, alone or in combination with other cytokines, is/are employed to proliferate and/or differentiate mammalian satellite cells into myoblasts. The present invention is also directed to a cell activating composition and a pharmaceutical composition comprising LIF alone or in combination with other cytokines to promote proliferation and/or differentiation of mammalian satellite cells in vitro and in vivo, respectively.

32 Claims, 9 Drawing Sheets

LOG LIF (UNITS)

DAYS: 1 D2 2 D5 3 D8 4 D11

DAYS
A, L0; B, L3; C, L10; D, L30; E, L100; (UNITS/ML)

Fig.2.

DAYS
A, T0: B, T0.3: C, T1.0: D, T3.0: E, T10 (ng/ml)

Fig.3.

FIG. 4A [FCS 0%]
FIG. 4B [FCS 1%]
FIG. 4C [FCS 2%]
FIG. 4D [FCS 5%]

[LIF]: 0U/ml  30 U/ml  100 U/ml

FIG. 4E
[FCS 7.5%]

FIG. 4F
[FCS 10%]

FIG. 4G
[FCS 15%]

FIG. 4H
[FCS 20%]

[LIF]: 0U/ml   30 U/ml   100 U/ml

PROLIFERATIVE ACTION OF LEUKAEMIA INHIBITORY FACTOR ON SATELLITE CELLS

The present invention relates to the use of leukaemia inhibitory factor (LIF), alone or in combination with other cytokines such as interleukin-6 (IL-6) and/or transforming growth factor α (TGFα) and/or fibroblast growth factor (FGF), to stimulate the proliferation and/or differentiation of mammalian satellite cells. The present invention also contemplates a method comprising myoblast transfer therapy whereby LIF, alone or in combination with other cytokines, is/are employed to proliferate and/or differentiate mammalian satellite cells into myoblasts. The present invention is also directed to a cell activating compositon and a pharmaceutical composition comprising LIF alone or in combination with other cytokines to promote proliferation and/or differentiation of mammalian satellite cells in vitro and in vivo, respectively.

Skeletal muscle consists of parallel arrays of multinucleated cells which are innervated and attached to bone through tendons. Although these highly differentiated cells are not capable of replication, muscle has a high capacity for regeneration after injury or disease and this is achieved by the activation of stem cells, called satellite cells, which lie in close association with muscle fibres. It has been estimated that up to 20% of muscle cell nuclei are found in satellite cells.

On activation, satellite cells differentiate into elongated mononuclear myoblasts. These, when in sufficient numbers, fuse to form multinucleated myotubes, the progenitor of the muscle fibre.

Primary cultures of muscle cells all originate from the satellite cells. The muscle is minced and treated with trypsin to break up fibres and extracellular matrix. Satellite cells, released as a result of this process, are harvested and placed under cell culture conditions.

After a lag period of about three days, the cells proliferate and undergo differentiation into myoblasts. These also proliferate and when the culture reaches confluence, the cells begin to fuse to form multinucleated myotubes. The cells may be passaged many times, but this must be done at the myoblast stage, before fusion.

The nature of the control of proliferation of satellite cells and subsequent differentiation into myoblasts is not well known although it has been discovered that the heparin binding growth factor, fibroblast growth factor (FGF), stimulates growth of satellite cells (Di Mario and Stohman, *Differentiation* 39:42–49, 1988).

The present invention arose in part from a study into the effect of a variety of cytokines on the early stages of muscle cell growth in culture. In accordance with the preset invention, it has been discovered that LIF and to a lesser extent other cytokines such as IL-6 and TGFα, stimulate the proliferation of satellite cells and the subsequent development of myoblasts.

Accordingly, one aspect of the present invention relates to a method of stimulating the proliferation and/or differentiation of mammalian satellite cells into myoblasts which method comprises contacting said cells with a stimulation-effective amount of LIF for a time and under conditions sufficient for said satellite cells to proliferate and/or differentiate into myoblasts.

Another aspect of the present invention relates to a method of stimulating the proliferation and/or differentiation of mammalian satellite cells into myoblasts which method comprises contacting said cells with a stimulation-effective amount of LIF in simultaneous or sequential combination with one or more other cytokines, for a time and under conditions sufficient for said satellite cells to proliferate and/or differentiate into myoblasts.

Still another aspect of the present invention contemplates a method of myoblast transfer therapy comprising contacting mammalian satellite cells with a proliferation- and/or differentiation- effective amount of LIF for a time and under conditions sufficient for said satellite cells to proliferate and/or differentiate into myoblasts and then administering said myoblasts at multiple sites into muscles. In an alternative to this embodiment, LIF is used in simultaneous or sequential combination with one or more other cytokines.

Yet another aspect of the present invention relates to a cell activating composition comprising LIF in combination with one or more other cytokines, and one or more physiologically acceptable carriers and/or diluents.

Still yet another aspect of the present invention relates to the use of LIF, alone or in combination with one or more other cytokines, in the manufacture of a cell activating composition for stimulating the proliferation and/or differentiation of mammalian satellite cells into myoblasts.

In still yet another aspect of the present invention there is provided a pharmaceutical composition for stimulating the proliferation and/or differentiation of satellite cells comprising LIF and one or more other cytokines and one or more pharmaceutically acceptable carriers and/or diluents.

In one preferred embodiment, the cytokines in optional combination with LIF include IL-6 and/or TGFα and/or FGF.

The satellite cells and cytokines may originate from homologous or heterologous mammals. If the same mammal is used, satellite cells and cytokines may originate from the same or different species of the same mammal. Mammals contemplated herein include but are not limited to humans, mice and livestock animals.

The present invention extends to naturally occurring (native), recombinant and/or synthetic cytokines and/or to their derivatives and/or analogues and/or to any combinations thereof. For example, recombinant murine and human LIF are disclosed in International Patent Application No. PCT/AU 88/00093. Use of the term "LIF" herein encompasses all such forms of LIF and its derivatives and analogues and includes single or multiple amino acid substitutions, deletions and/or additions to the polypeptide portion of the LIF molecule and single or multiple substitutions, deletions and/or additions to the carbohydrate portion of the molecule (when present). Derivatives and analogues of LIF include portions of native, recombinant and/or synthetic LIF which have the desired activity.

By "simultaneous or sequential combination" as used herein means the addition of LIF and one or more other cytokines at the same time, i.e. in a single composition or the administration of each active molecule or groups thereof one after the other. By way of non-limiting example, LIF may be used first followed by a second cytokine followed by a third cytokine and so on. Alternatively, LIF may be used first followed by a combination of other cytokines. In another embodiment, other cytokines are used first (simultaneously or sequentially), followed by LIF.

The present invention is of medical significance especially in relation to primary, genetically determined, muscle myopathies. There are considerable numbers of these, the most severe and the most common of which, being Duchenne muscular dystrophy (DMD). The affected gene is known and its protein product has been deduced. The protein product, dystrophin, is probably a a component of the cytoskeleton, membrane linkage. It is large, 425,000 daltons, and the gene is the largest of the human genes. Because of its complexity, it is unlikely that genetic manipulation will be possible in the near future. However, another approach has been shown to be effective in mouse models of muscular dystrophies, including the mdx mouse.

This approach involves the growing of myoblasts in culture derived from normal mice and injecting them, at multiple sites, into muscles of mutant mice. The results have shown that not only has rejection been minimal, but the muscles contain dystrophin whereas previously there was none.

In a mouse strain showing very severe muscle wastage (not dystrophin deficient, but a mutant with an unknown defect) muscle strength returned to near normal.

Thus, a procedure is contemplated termed myoblast transfer therapy, whereby human myoblasts, grown in culture, are injected at multiple sites into muscles of DMD. This approach is applicable to all primary myopathies and not only DMD.

The process involves injection of many myoblasts at multiple sites in a large number of muscles. It is time-consuming and the cost of myoblast culture is high. At present, techniques of culturing myoblasts utilize medium to long term culture with varying concentrations of the expensive reagent feotal calf serum (FCS). Thus, any factor which may accelerate the myoblast differentiation and growth should be significant in reducing the cost of myoblast production. In accordance with the present invention, therefore, LIF alone, or in combination with other cytokines such as IL-6 and/or TGF$\alpha$ and/or FGF, will fulfill this need.

Accordingly, one aspect of the present invention is directed to a method of stimulating the proliferation and/or differentiation of mammalian satellite cells into myoblasts comprising contacting said satellite cells with a stimulation-effective amount of LIF, alone or in combination with other cytokines such as IL-6 and/or TGF$\alpha$ and/or FGF, for a time and under conditions sufficient to stimulate the satellite cells.

The present invention is also directed to cell activating compositions comprising LIF with or without other cytokines such as IL-6 and/or TGF$\alpha$ and/or FGF and one or more physiologically acceptable carriers and/or diluents. Preferably, the compositions comprise LIF in combination with one or more other cytokines.

The present invention is also directed to a pharmaceutical composition for stimulating the proliferation and/or differentiation of mammalian satellite cells which composition comprises LIF with one or more other cytokines and one or more pharmaceutically acceptable carriers and/or diluents. In one embodiment, the cytokines other than LIF contemplated herein include IL-6 and/or TGF$\alpha$ and/or FGF. Methods for preparing a pharmaceutical composition are known in the art such as described in *Remington's Pharmaceutical Sciences* 16th ed., 1980, Mach Publishing Co., edited by Osol et al. and hereby incorporated by reference. The route of administration and the effective amount of active component will be determined by the situation but one preferred route is intramuscular although other routes of administration may be employed. For the purposes of exemplification of this embodiment of the present invention, the effective amount of LIF used is from about 0.1 to about 1000 U/ml, preferably about 1 to about 100 U/ml and most preferably from about 10 to about 50 U/ml. A unit of LIF is defined in PCT/AU 88/00093. In general, other cytokines will be used at from about 1 to about 100 ng/ml. More specifically, IL-6 may be preferably used at a concentration of about 60 to about 100 ng/ml; TGF$\alpha$ preferably at about 1 to about 20 ng/ml; and FGF preferably at about 20 to about 50 ng/ml. These concentrations may vary depending on the circumstances and it is not the intention to necessarily limit the present invention to these effective amounts.

The present invention is further described by the following non-limiting Figures and Examples. In the Figures:

FIGS. 5A–5C are photographic representations showing fusion of LIF-supported myoblasts in culture. Human myoblasts were grown either in the absence or presence of 30 units/ml LIF. These were harvested, suspended in PBS and injected into one extensor digitorum longus of mdx mice. The mice were killed 5 weeks later and the muscle was embedded for cryostat sectioning. Sections were treated with anti-dystrophin antibodies and the presence of dystrophin was visualised using fluorescein labelled anti-sheep antibodies. (A) Muscle of C57-BL-10 normal, dystrophin positive mouse. (B) Muscle of non-injected mdx, dystrophin negative mouse. (C) Muscle from mdx mouse injected with myoblasts grown in the presence of LIF. Note patches of dystrophin—positive areas underlying the sarcolemma.

EXAMPLE 1

Materials and Methods

Mouse muscle cells

The muscle used was from the hind legs of mouse strain C57-BL-10. A mutant from the same strain was also used. This is a mdx mutant in which the muscle protein dystrophin is missing. This is an excellent model to study muscular dystrophy since the same gene is affected in the human condition.

Primary cultures of these cells were grown as described by Gurusingha et al. *Muscle and Nerve* 11: 1231-1239, 1988, except that 5-10% v/v FCS was used. When at about 80% confluence, the cells were washed briefly with PBS and treated with 0.025% w/v trypsin in dissociation buffer to detach them. Foetal calf serum (FCS) was added to 5% v/v concentration to inhibit the trypsin, the cells centrifuged at 1000 rpm for 10 minutes and washed twice with PBS. They were then plated at 10% confluence in Ham F12, 20% v/v FCS to provide passaged cells.

Human muscle cells

Under these conditions, many cells survive and differentiate, but at a rate lower than those under optimum conditions in which 20% (v/v) FCS is used. Usually there is a lag period of 3-4 days during which time cell numbers tend to decrease followed by the appearance of myoblasts at day 5-7. The cells are initially plated into 96 well cluster plates at a density of 3-5000 cells/well. Growth factors are added 3 days after initiation of the culture and the effect quantitated by counting cells as satellite cells or myoblasts over a period. Samples (0.5-1.5 g) of human skeletal muscle were removed by collaborating surgeons from consenting patients during operative procedures. Human Ethics Committee Approvals are held from Monash University, the Monash Medical Centre, Clayton and the Royal Children's Hospital, Parkville. These samples were transported back to the laboratory and cultures commenced, essentially as described for mouse cells.

In vivo Satellite Cells transfer

Passaged mouse or human myoblasts were grown to 80-90% confluence in the absence or presence of 30 units/ml LIF and harvested as described above. They were suspended in PBS at $3 \times 10^8$ cells/mi. Mutant mdx mice, 25-32 days of age were anaesthetised by I.P. injection of a mixture of hypnorm (0.3 ml/kg) and diazapam (5 mg/kg). One extensor digitorum longus (EDL) muscle was exposed and myoblasts were injected. These cells were delivered in 1 μl lots from a SGE syringe fitted with a needle that had been electropolished at the tip to 27 gauge. The syringe was mouted on a micromanipulator to control position and depth of injection. Four or five injections were made into each muscle, at intervals of 1.5-2 mm. Control injections were carried out using PBS alone. The wound was sutured and the mouse allowed to recover.

After 4 to 6 weeks, the animals were killed by breaking the neck, the EDL muscle re-exposed, cooled with ice cold PBS, removed and embedded in Tissue—Tek OCT and immediately quenched in isopentane at liquid $N_2$ temperature. The blocks were trimmed at −25° and transverse sections cut in a cryostat at −20° to 3-4 μm. When air-dried, the sections were treated with either 60 Kd or 30 Kd anti-dystrophin antibodies (Hoffman et al. *Cell* 51: 919-928, 1987) diluted 1/200 with PBS. Pre-immune serum was similarly diluted. After incubation at R.T. for 30 minutes at 100% humidity, the sections were washed three times and then subjected to FITC donkey—antisheep antibodies (Silenius, Melbourne) at 1/40 dilution. They were again washed and mounted under coverslips.

EXAMPLE 2

Mouse Myoblasts

Primary cultures of mouse myoblasts were passaged and grown in medium containing LIF at various concentrations. This procedure was carried out three times in medium containing 5%, 7.5% and 10% v/v FCS. Thus, it was possible to test whether passaged cells respond to LIF in the same manner as primary cultures and also to examine the response to LIF under various growth conditions.

Figure 1A:
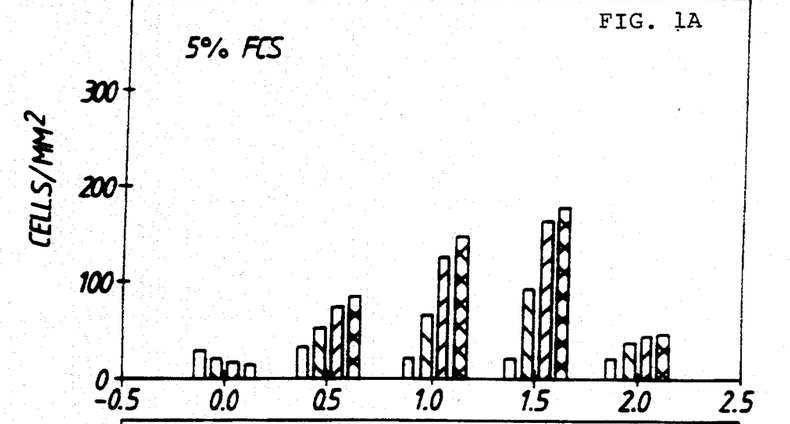
FIGS. 1A–1C are graphical representations response of passaged cells to LIF at several concentrations of FCS. Passaged mouse myoblasts (P2) were plated into 96 well plates at 2500 cells per well, in Ham F12 medium containing 5, 7.5 or 10% v/v FCS. LIF was added at the concentrations shown and the cell grown without further change of medium. Cell numbers were counted at the times shown and are expressed as cells/mm$^2$ of well surface.
Figure 1B:
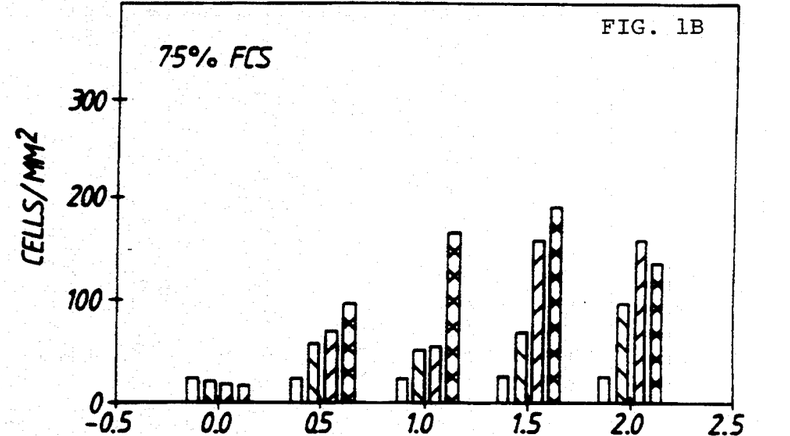
Figure 1C:
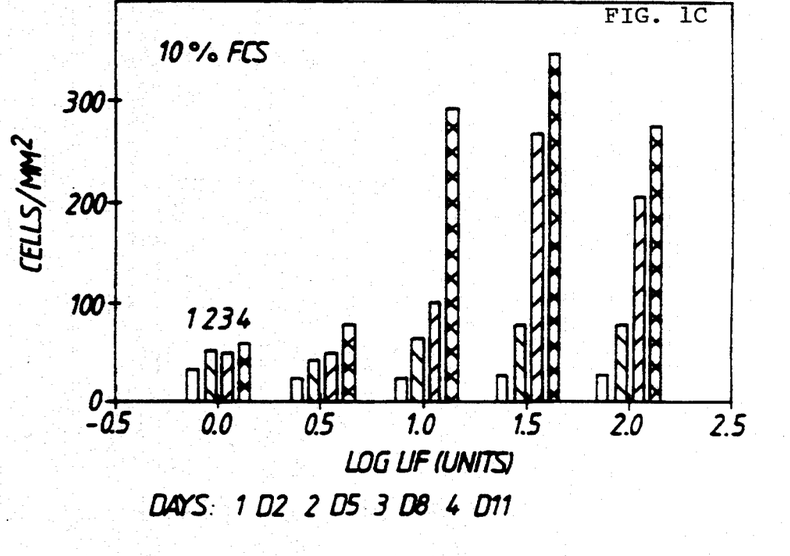

FIGS. 1A-1C show that passaged mouse cells respond to LIF at several cell concentrations of FCS. The optimum concentration of LIF is 30 units/ml (14 pg/ml) as it was for primary cultures. There was a greater effect of LIF at 10% v/v FCS concentration than at lower concentrations, this being a 13 fold increase over controls.

Human myoblasts

Figure 2:
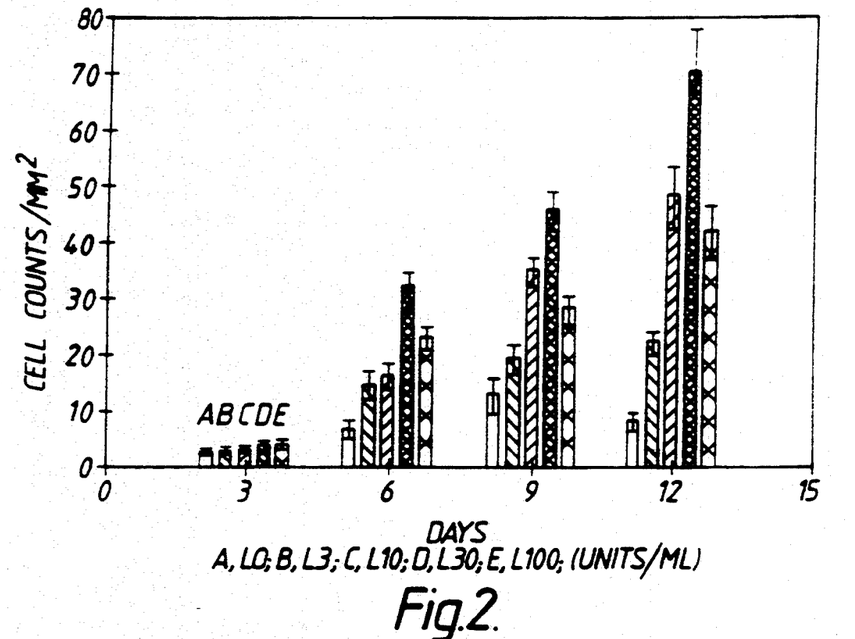
FIG. 2 is a graphical representation showing the effect of LIF on human myoblasts. Human myoblasts were derived from a sample of human skeletal muscle, grown to about 80% confluence and passaged. These passaged cells were grown in the presence of LIF, as described for FIG. 1.

These cells were grown from donor human muscle and passaged cells were seeded at 2-3000 cells per well in a 96 well cluster plate in Ham F12 medium containing 7.5% v/v FCS as was carried out for initial mouse cell cultures. The medium contained varying concentrations of LIF. Cell numbers were counted at times up to 12 days and the results are shown in FIG. 2. As with mouse cells, there was a marked stimulation of proliferation of myoblasts by LIF. Again the optimum concentration found for LIF was 30 units/mi. This shows that human myoblasts respond to LIF in a manner similar to mouse myoblasts.

Figure 3:
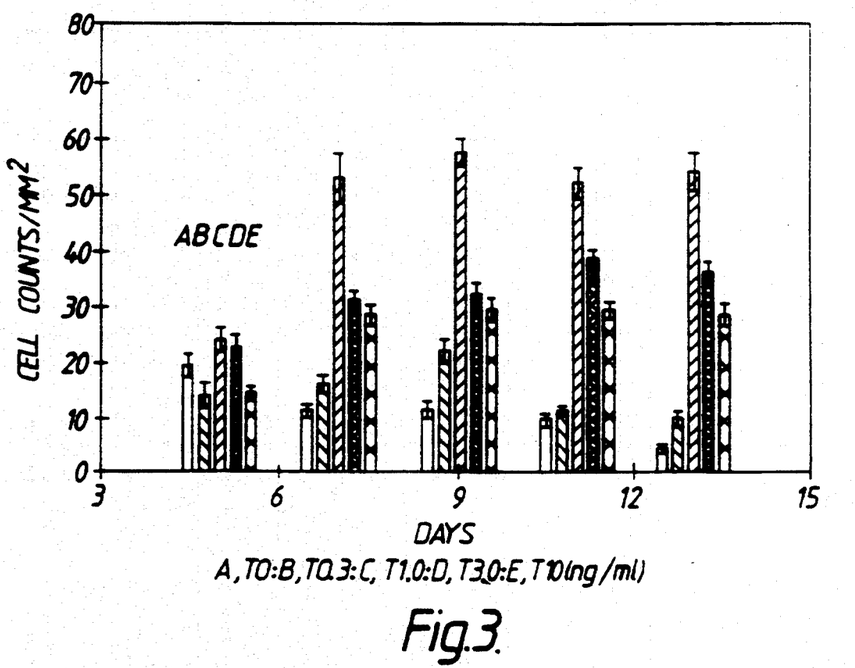
FIG. 3 is a graphical representation showing the effect of TGF-$\alpha$ replaced LIF at the concentrations shown.
Figure 4A:
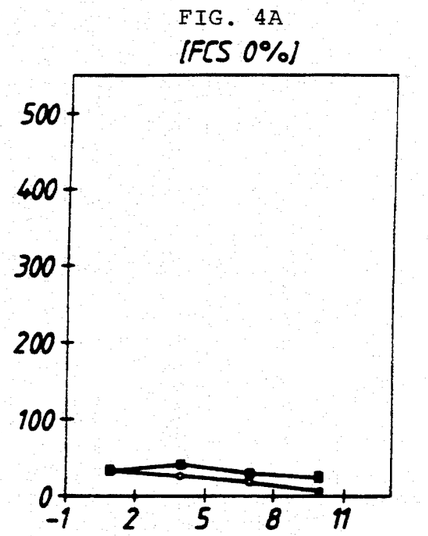
FIGS. 4A–4H are graphical representations showing the effect of FCS concentration of LIF activity. LIF and FCS human myoblasts were grown as described for FIG. 2. FCS, ranging from 0 to 20% v/v was added to the Ham F12 medium before addition of LIF. (a) 0% –5% v/v FCS, (b) 7.5% –20% v/v FCS.
Figure 4B:
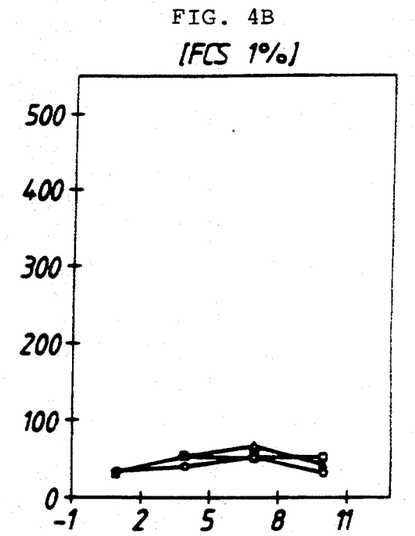
Figure 4C:
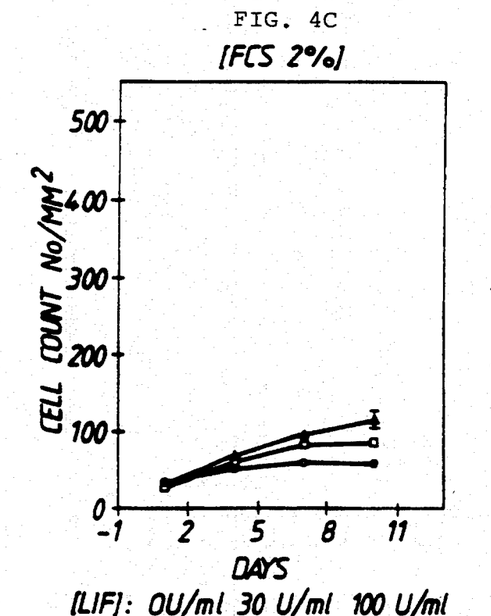
Figure 4D:
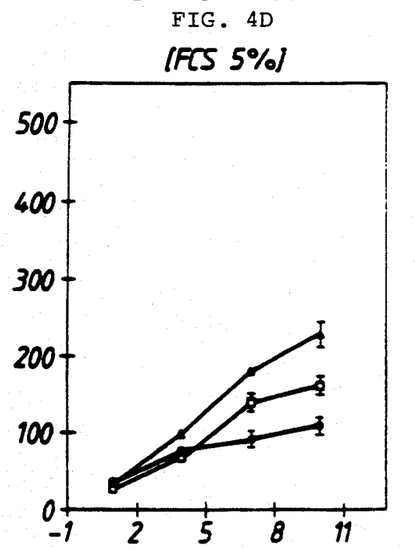
Figure 4E:
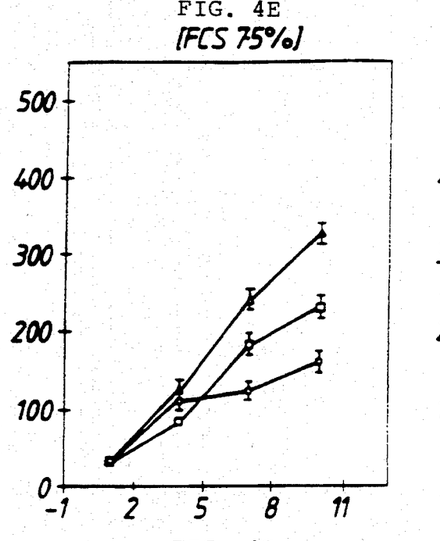
Figure 4F:
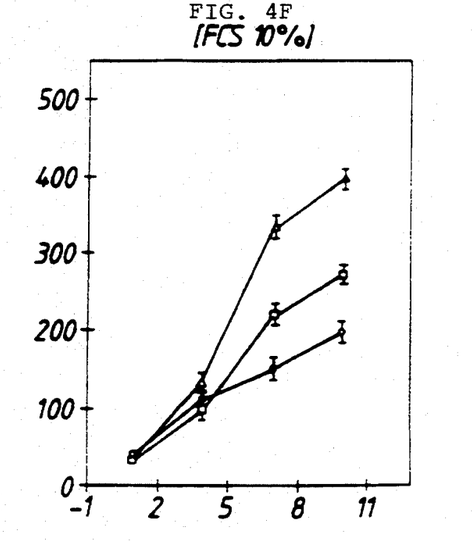
Figure 4G:
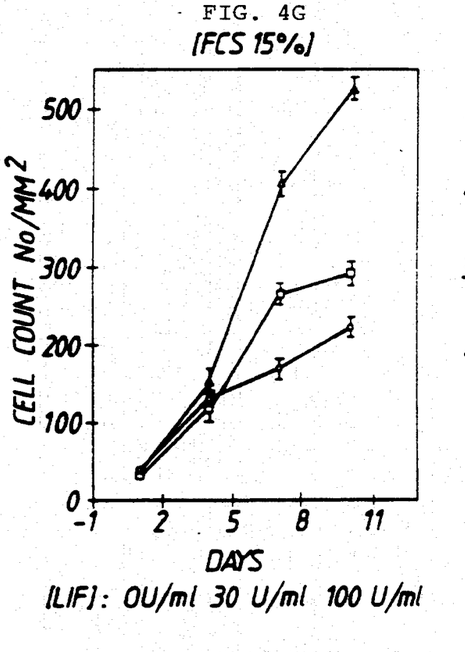
Figure 4H:
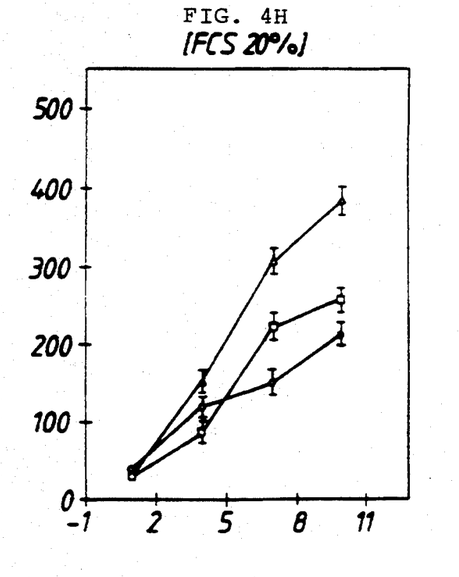

It has previously been found that TGF-α also stimulates mouse myoblasts. Human cells were grown also in the presence of this cytokine at concentrations ranging up to 10 ng/ml. FIG. 3 shows that there was early response to TGF-α, with an optimum concentration of 1 ng/ml, the same as that found for mouse cells. As was the case for LIF, higher concentrations were less effective than that at the optimum. Unlike mouse cells, the response occurred early. This may be due to species differences or passaging of cells or some other unknown factors.

Effects of FCS concentrations of LIF activity

Passaged human myoblasts were grown in Ham F12 medium containing FCS concentrations ranging from 0-20% v/v FCS. At each of the FCS concentrations, LIF was added at 0, 30 or 100 units/mi. FIGS. 4A-4H show that at 0 and 1% v/v FCS there is no cell growth in the absence or presence of LIF. When the FCS concentration is 2% v/v, again there is no growth in the absence of LIF, but some growth occurs in its presence. At increasing concentrations of FCS, LIF provides increased growth and as shown previously, 30 units/ml of LIF is more effective that 100 units/ml, at all FCS levels. Optimum stimulation of growth by LIF was found to occur at 15% v/v FCS.

In vivo myoblast transfer

Figure 5A:
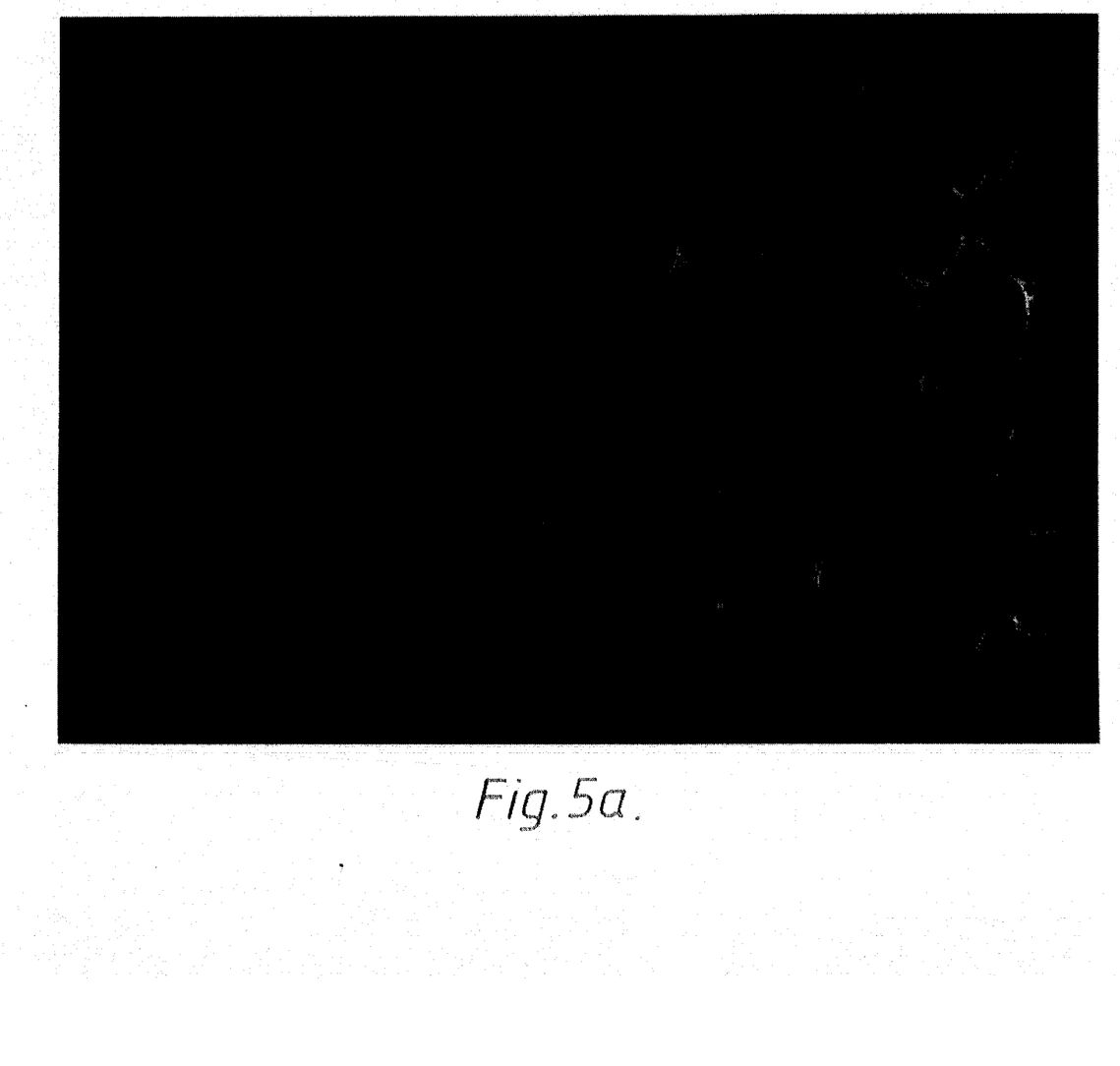
Figure 5B:
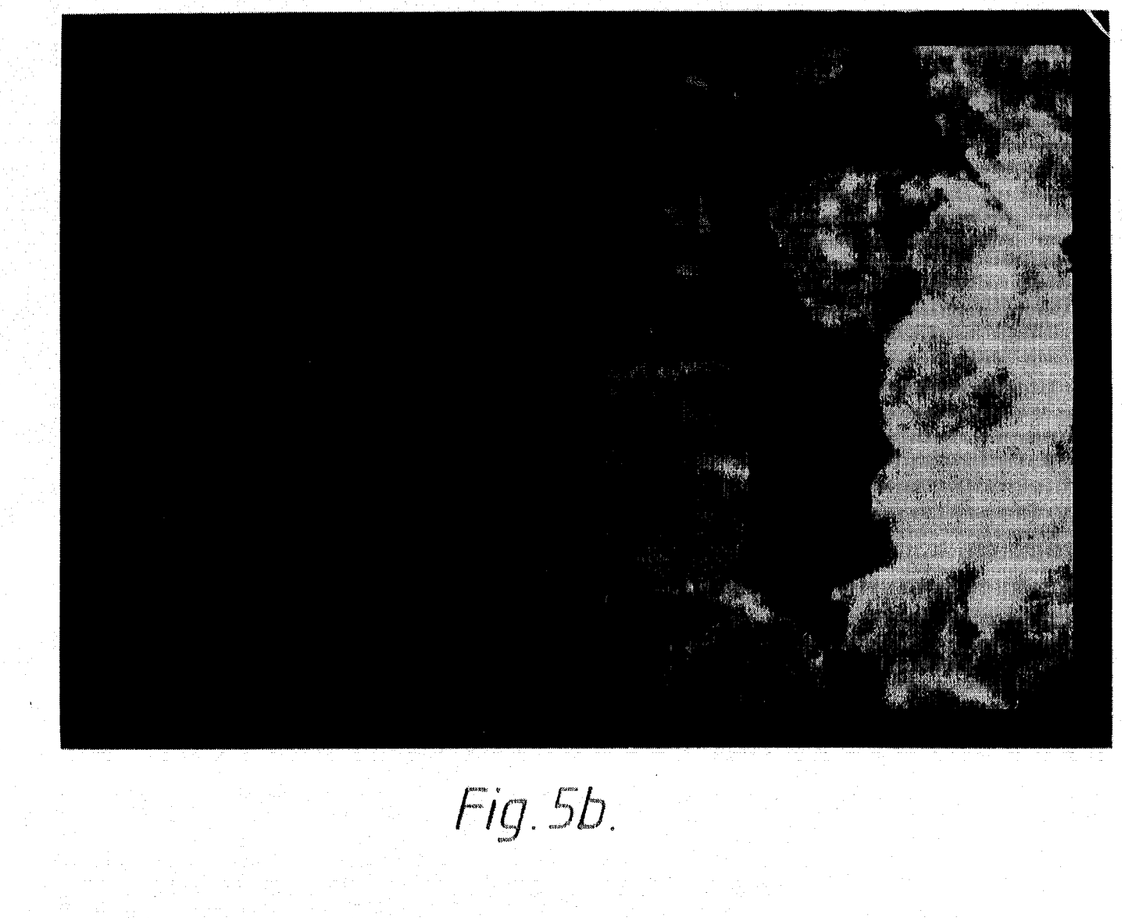

Mice were injected with either mouse or human myoblasts cultured in the presence of LIF as described in Example 1 at the rate of 1–1.5×10⁶ cells per EDL muscle. These were killed and the muscles prepared for immuno cytochemistry 4–6 weeks later. FIG. 5A shows the presence of dystrophin in an EDL muscle of the C57-BL-10 dystrophin positive control mouse strain. As described by others (Partridge et al. *Nature* 337: 176–179, 1989) the dystrophin is located under the surface of the sarcolemma membrane. The mdx dystrophin negative muscle is shown in FIG. 5B. No immunoreaction is evident.

Figure 5C:
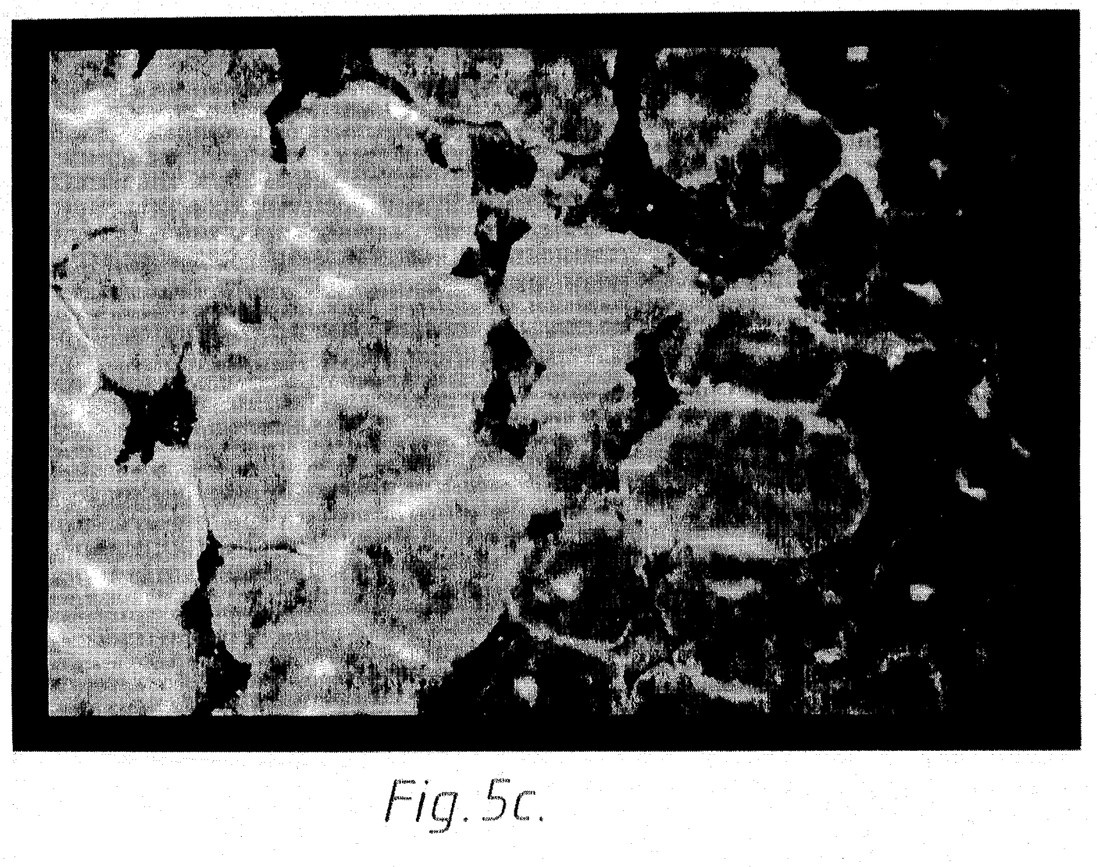

FIG. 5C shows EDL muscle sections from an mdx mouse injected 6 weeks earlier with human myoblasts. That fusion has occurred can be seen from dystrophin positive patches located at the sarcolemma of the fibres. Positive fusion was also found when mouse myoblasts were injected into the EDL muscles.

LIF receptors on myoblasts

Figure 6A:
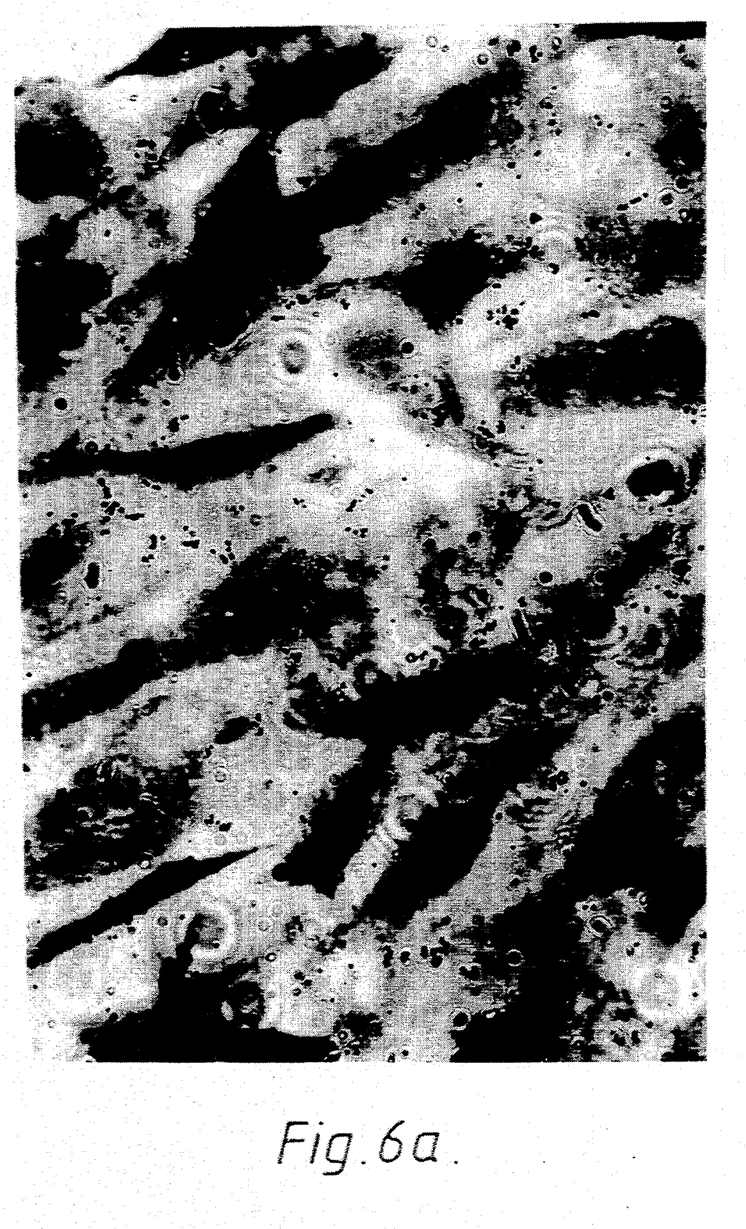
FIGS. 6A and 6B are photographic representations showing LIF receptors on myoblasts. Autoradiography of mouse myoblasts subjected to $^{125}$I-LIF. (a) $^{125}$I-LIF alone. (b) $^{125}$I-LIF in the presence of a 1000-fold excess of non-labelled LIF.
Figure 6B:
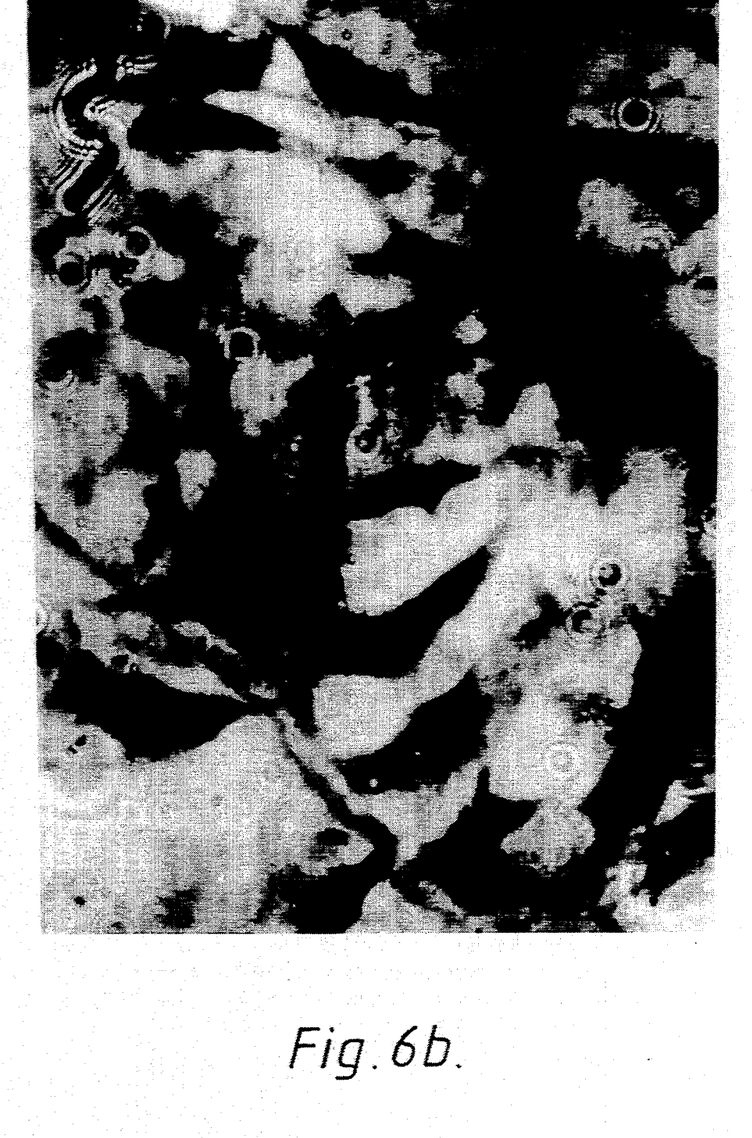

Mouse myoblasts were grown on glass slides, pretreated with fibronectin to ensure good adhesion. After eight days in culture, they were subjected to $^{125}$I-labelled LIF in the absence and present of a 1000 fold excess of unlabelled LIF. FIG. 6A shows that LIF receptors are present on myoblasts, whereas FIG. 6B shows low non-specific binding.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

I claim:

1. A method of stimulating the proliferation and differentiation of mammalian satellite cells into myoblasts which method comprises contacting said cells with a stimulation-effective amount of leukaemia inhibitory factor (LIF) for a time and under conditions sufficient for said satellite cells to proliferate and differentiate into myoblasts.

2. The method according to claim 1 which further comprises the addition of one or more other cytokines in simultaneous or sequential combination with LIF.

3. The method according to claim 1 wherein the LIF, and satellite cells are from the same mammal.

4. The method according to claim 1 wherein the LIF and satellite cells are from the same species of mammal.

5. The method according to claim 1 wherein the LIF and satellite cells are from different mammals.

6. The method according to any one of claims 1 to 5 wherein the mammal is human, mouse or a livestock animal.

7. The method according to claim 1 wherein the LIF is prepared by recombinant or synthetic means.

8. The method according to claim 2 wherein the cytokine is one or more of IL-6, TGFα and/or FGF.

9. The method according to claim 1 or 2 wherein LIF is provided at a concentration of from about 0.1 to about 1000 U/ml and the cytokine is provided at a concentration of from about 1 to about 100 ng/ml.

10. The method according to claim 9 wherein LIF is provided at a concentration of from about 1 to 100 U/ml.

11. The method according to claim 10 wherein LIF is provided at a concentration of from about 10 to about 50 U/ml.

12. The method according to claim 2 wherein said LIF, said cytokine and said satellite cells are from the same mammal.

13. The method according to claim 2 wherein said LIF, said cytokine and said satellite cells are from the same species of mammal.

14. The method according to claim 2 wherein at least two of said LIF, said cytokine and said satellite cells are from different mammals.

15. The method according to claim 2 wherein said cytokine is prepared by recombinant or synthetic means.

16. A method of myoblast transfer comprising contacting mammalian satellite cells with a proliferation- and differentiation-effective amount of LIF for a time and under conditions sufficient for said satellite cells to proliferate and differentiate into myoblasts and then administering said myoblasts at multiple sites into muscles.

17. The method according to claim 16 which further comprises the addition of one or more other cytokines in simultaneous or sequential combination with LIF.

18. The method according to claim 16 wherein the LIF, and satellite cells are from the same mammal.

19. The method according to claim 16 wherein the LIF and satellite cells are from the same species of mammal.

20. The method according to claim 16 wherein the LIF satellite cells are from different mammals.

21. The method according to claim 17 wherein said LIF, said cytokine and said satellite cells are from the same mammal.

22. The method according to claim 17 wherein said LIF, said cytokine and said satellite cells are from the same species of mammal.

23. The method according to claim 17 wherein at least two of said LIF, said cytokine and said satellite cells are from different mammals.

24. The method according to any one of claims 16 to 20 and 21 to 23, wherein the mammal is human, mouse or a livestock animal.

25. The method according to any one of claims 17 and 21 to 23 wherein the cytokine is one or more of IL-6, TGFα and/or FGF.

26. The method according to any one of claims 16 to 20 and 21 to 23 wherein LIF is provided in a concentration of from about 0.1 to about 1000 U/ml and the cytokine is provided at a concentration of from about 1 to about 100 ng/ml.

27. The method according to claim 26 wherein LIF is provided at a concentration of from about 1 to about 100 U/ml.

28. The method according to claim 27 wherein LIF is provided at a concentration of from about 10 to about 50 U/ml.

29. The method according to any one of claims 16 to 20 and 21 to 23 wherein the myoblasts so obtained are administered by intramuscular injection.

30. The method according to claim 16 wherein the LIF is prepared by recombinant or synthetic means.

31. The method according to claim 17 wherein said cytokine is prepared by recombinant or synthetic means.

32. A pharmaceutical composition comprising LIF and at least one of IL-6, TGFα and FGF, and a pharmaceutically acceptable carrier.

* * * * *

UNITED STATES PATENT AND TRADEMARK OFFICE
CERTIFICATE OF CORRECTION

PATENT NO. : 5,435,999
DATED : July 25, 1995
INVENTOR(S) : Lawrence Austin

It is certified that error appears in the above-indentified patent and that said Letters Patent is hereby corrected as shown below:

Column 4, line 13: "TGFαpreferably" should read --TGFα preferably--

Column 4, line 39: "TGF-αreplaced" should read --TGF-α replaced--

Column 5, line 43: "In vivo Satellite Cells transfer" should read --In vivo myoblast transfer:--

Column 5, line 47: "mi." should read --ml.--

Column 6, lines 38 & 58: "mi." should read --ml.--

Column 6, line 42: "TGF-αalso" should read --TGF-α also--

Signed and Sealed this

Eleventh Day of June, 1996

Attest:

BRUCE LEHMAN

*Attesting Officer*  *Commissioner of Patents and Trademarks*